United States Patent
Schennum (10) Patent No.: US 8,495,998 B2
(45) Date of Patent: Jul. 30, 2013

(54) INHALER

(75) Inventor: Steven Michael Schennum, Plainfield, IL (US)

(73) Assignee: British American Tobacco (Investments) Limited, London (GB)

( * ) Notice: Subject to any disclaimer, the term of this patent is extended or adjusted under 35 U.S.C. 154(b) by 1078 days.

(21) Appl. No.: 12/486,476

(22) Filed: Jun. 17, 2009

(65) Prior Publication Data

US 2010/0319686 A1    Dec. 23, 2010

(51) Int. Cl.
*A61M 15/06*    (2006.01)

(52) U.S. Cl.
USPC ............ 128/200.23; 128/200.24; 128/201.28; 128/200.17

(58) Field of Classification Search
USPC ............. 128/200.14, 200.24, 200.11, 200.16, 128/200.21, 201.25
See application file for complete search history.

(56) References Cited

U.S. PATENT DOCUMENTS

| | | | |
|---|---|---|---|
| 2,445,476 A | 7/1948 | Folkman |
| 2,470,296 A | 5/1949 | Fields |
| 2,479,002 A | 8/1949 | Ceperly |
| 2,513,145 A | 6/1950 | Chapple |
| 2,534,636 A | 12/1950 | Stirn |
| 2,587,215 A | 2/1952 | Priestly |
| 2,603,215 A | 7/1952 | Arnow |
| 2,642,063 A | 6/1953 | Brown |
| 2,721,551 A | 10/1955 | Lobl |
| 2,809,634 A | 10/1957 | Murai |
| 2,830,597 A | 4/1958 | Kummli |
| 2,860,638 A | 11/1958 | Bartolomeo |
| 3,157,179 A | 11/1964 | Paullus et al. |
| 3,404,692 A | 10/1968 | Lampert |
| 3,565,071 A | 2/1971 | Katerndahl et al. |
| 3,631,856 A | 1/1972 | Taylor |
| 3,683,936 A | 8/1972 | O'Neil |

(Continued)

FOREIGN PATENT DOCUMENTS

| | | |
|---|---|---|
| DE | 3639667 A1 | 6/1988 |
| EP | 0295122 B1 | 1/1992 |

(Continued)

OTHER PUBLICATIONS

International Search Report and Written Opinion, mailed Jul. 21, 2010, for PCT International Application No. PCT/EP2010/056623, filed May 13, 2010.

(Continued)

*Primary Examiner* — Jerome w Donnelly
(74) *Attorney, Agent, or Firm* — NW Poulsen (57) ABSTRACT

A portable, handheld breath-actuated inhaler comprises a generally cylindrical body that comprises body portions 1, 3 that receive a canister 2 of pressured fluid such a nicotine to be inhaled in an aerosol by a user, a mouthpiece 7 in the first body portion 1 configured to deliver an amount of the aerosol to the mouth of the user from the canister. A trigger is cocked ready for releasing pressurized fluid from the canister by manually sliding the body portions 1, 3 towards one another. The trigger comprises a compression spring 26 and a cam 33 which engages a pressure sensitive puff lever 28 with a plate 29 that releases the cocked trigger when a user sucks on the mouthpiece and draws in air through air inlet opening 26. Release of the trigger releases spring 26 which slides the body portions apart and also opens a valve in the canister so as to deliver the aerosol to the mouthpiece.

36 Claims, 7 Drawing Sheets

U.S. PATENT DOCUMENTS

| | | |
|---|---|---|
| 3,721,240 A | 3/1973 | Tamburri |
| 4,083,372 A | 4/1978 | Boden |
| 4,171,000 A | 10/1979 | Uhle |
| 4,284,089 A | 8/1981 | Ray |
| 4,393,884 A | 7/1983 | Jacobs |
| 4,429,703 A | 2/1984 | Haber |
| 4,635,651 A | 1/1987 | Jacobs |
| 4,648,393 A * | 3/1987 | Landis et al. ............ 128/200.23 |
| 4,715,387 A | 12/1987 | Rose |
| 4,735,217 A | 4/1988 | Gerth |
| 4,765,347 A | 8/1988 | Sensabaugh et al. |
| 4,765,348 A | 8/1988 | Honeycutt |
| 4,774,971 A | 10/1988 | Vieten |
| 4,793,366 A | 12/1988 | Hill |
| 4,800,903 A | 1/1989 | Ray et al. |
| 4,813,437 A | 3/1989 | Ray |
| 4,892,109 A | 1/1990 | Strubel |
| 4,945,929 A | 8/1990 | Egilmex |
| 4,993,436 A | 2/1991 | Bloom |
| 4,995,407 A | 2/1991 | Kossiakoff et al. |
| 5,101,838 A | 4/1992 | Schwartz et al. |
| 5,167,242 A | 12/1992 | Turner et al. |
| 5,176,132 A | 1/1993 | Drought et al. |
| 5,284,163 A | 2/1994 | Knudsen |
| 5,287,850 A | 2/1994 | Haber et al. |
| 5,293,883 A | 3/1994 | Edwards |
| 5,327,915 A | 7/1994 | Porenski et al. |
| 5,400,808 A | 3/1995 | Turner et al. |
| 5,441,060 A | 8/1995 | Rose et al. |
| 5,501,236 A | 3/1996 | Hill et al. |
| 5,522,380 A * | 6/1996 | Dwork .................... 128/200.23 |
| 5,535,735 A | 7/1996 | McPherson |
| 5,687,746 A | 11/1997 | Rose et al. |
| 5,743,251 A | 4/1998 | Howell et al. |
| 5,746,227 A | 5/1998 | Rose et al. |
| 5,799,663 A | 9/1998 | Gross et al. |
| 5,893,371 A | 4/1999 | Rose et al. |
| 5,894,841 A | 4/1999 | Voges |
| 5,954,047 A * | 9/1999 | Armer et al. ............ 128/200.23 |
| 6,024,097 A | 2/2000 | Von Wielligh |
| 6,041,789 A | 3/2000 | Bankert et al. |
| 6,082,355 A * | 7/2000 | Howlett .................. 128/200.23 |
| 6,085,745 A | 7/2000 | Levander et al. |
| 6,098,632 A | 8/2000 | Turner et al. |
| 6,155,251 A * | 12/2000 | Hauser .................... 128/200.23 |
| 6,196,218 B1 | 3/2001 | Voges |
| 6,216,705 B1 | 4/2001 | Ossepian |
| 6,234,169 B1 | 5/2001 | Bulbrook et al. |
| 6,443,146 B1 | 9/2002 | Voges |
| 6,491,233 B2 | 12/2002 | Nichols |
| 6,595,209 B1 | 7/2003 | Rose et al. |
| 6,595,210 B2 | 7/2003 | Ohki et al. |
| 6,606,992 B1 | 8/2003 | Schuler et al. |
| 6,606,998 B1 | 8/2003 | Gold |
| 6,637,430 B1 | 10/2003 | Voges et al. |
| 6,679,255 B2 | 1/2004 | Pera |
| 6,701,921 B2 | 3/2004 | Sprinkel, Jr. et al. |
| 6,772,755 B2 | 8/2004 | Pera |
| 6,804,458 B2 | 10/2004 | Sherwood et al. |
| 6,889,687 B1 | 5/2005 | Olsson |
| 7,013,888 B2 | 3/2006 | Hughes |
| 7,025,059 B2 | 4/2006 | Pera |
| 7,117,867 B2 | 10/2006 | Cox et al. |
| 7,131,599 B2 | 11/2006 | Katase |
| 7,467,630 B2 | 12/2008 | Childer et al. |
| 7,481,213 B2 | 1/2009 | Childers |
| 2002/0179101 A1 | 12/2002 | Chavez |
| 2003/0072717 A1 | 4/2003 | Reinhold et al. |
| 2003/0111088 A1 | 6/2003 | Fox |
| 2005/0016533 A1 | 1/2005 | Schuler et al. |
| 2006/0118128 A1 | 6/2006 | Hoffmann |
| 2006/0191546 A1 | 8/2006 | Takano |
| 2006/0196518 A1 | 9/2006 | Hon |
| 2006/0254604 A1 | 11/2006 | Fernandez |
| 2006/0283468 A1 | 12/2006 | Lipowicz |
| 2007/0062548 A1 | 3/2007 | Horstmann |
| 2007/0144512 A1 | 6/2007 | Evani |
| 2007/0175476 A1 | 8/2007 | Lipowicz |
| 2007/0267031 A1 | 11/2007 | Hon |
| 2007/0283972 A1 | 12/2007 | Monsees |
| 2008/0000487 A1 | 1/2008 | Valadi |
| 2008/0223362 A1 | 9/2008 | Hamano |
| 2008/0230052 A1 | 9/2008 | Montaser |
| 2008/0241255 A1 | 10/2008 | Rose et al. |
| 2008/0257367 A1 | 10/2008 | Paterno et al. |

FOREIGN PATENT DOCUMENTS

| | | |
|---|---|---|
| EP | 1154815 B1 | 7/2004 |
| EP | 1225942 B1 | 2/2005 |
| EP | 1618803 B1 | 12/2008 |
| EP | 1736065 B1 | 6/2009 |
| GB | 2292891 A | 3/1996 |
| JP | 11342204 A | 12/1999 |
| JP | 2004187658 A | 7/2004 |
| JP | 2006223158 A | 8/2006 |
| WO | 9209323 A1 | 6/1992 |
| WO | 0181182 A2 | 11/2001 |
| WO | 2007141520 A1 | 12/2007 |

OTHER PUBLICATIONS

International Preliminary Report on Patentability, mailed Jan. 5, 2012, for PCT International Application No. PCT/EP2010/056623, filed May 13, 2010.

* cited by examiner

INHALER

FIELD OF THE INVENTION

This invention relates to a portable, handheld breath-actuated inhaler which may be used to deliver a nicotine containing aerosol.

BACKGROUND

A nicotine dispensing aerosol device is disclosed in U.S. Pat. No. 4,945,929, which simulates a smoking article such as a cigarette, without having to burn tobacco.

SUMMARY

According to the invention, there is provided a portable, handheld breath-actuated inhaler comprising a body to receive a canister of pressured fluid to be inhaled in an aerosol by a user, a mouthpiece configured to deliver an amount of the aerosol to the mouth of the user, a trigger mechanism operable to be cocked into a configuration ready for releasing pressurized fluid from the canister, and a pressure sensitive member operable to release the cocked trigger in response to the user sucking on the body so as to deliver the fluid to the mouthpiece.

The body may include first and second parts moveable relative to one another to cock the trigger mechanism, and a spring to store energy upon cocking of the trigger mechanism.

The first and second parts of the body may be generally cylindrical about a common longitudinal axis so as to simulate the general appearance of a smoking article such as a cigarette or a cigar and the parts may be moveable axially relative to one another. One of the parts of the body may include a mouthpiece and the other may include the spring and trigger mechanism and be adapted to receive the canister.

The first and second parts of the body may be moveable towards one another to cock the trigger mechanism and compress the spring, and to move away from one another under the action of the spring when the trigger is released by the pressure sensitive member, resulting in an elongation of the body.

The body can include an inlet aperture to allow air to be drawn into the inhaler in response to sucking on the mouthpiece, so that the air is mixed with the aerosol fluid delivered from the canister into the mouthpiece. The pressure sensitive member may include a puff lever to at least partially cover the inlet aperture within the body, the puff lever being configured to be rotated by pressure differential caused by air drawn into the body when the user sucks on the mouthpiece, which results in release of the cocked trigger mechanism and the delivery of the aerosol fluid into the mouthpiece.

BRIEF DESCRIPTION OF THE DRAWINGS

In order that the invention may be more fully understood, embodiment thereof will now be described by way of illustrative example with reference to the accompanying drawings, in which.

DETAILED DESCRIPTION

Figure 1:
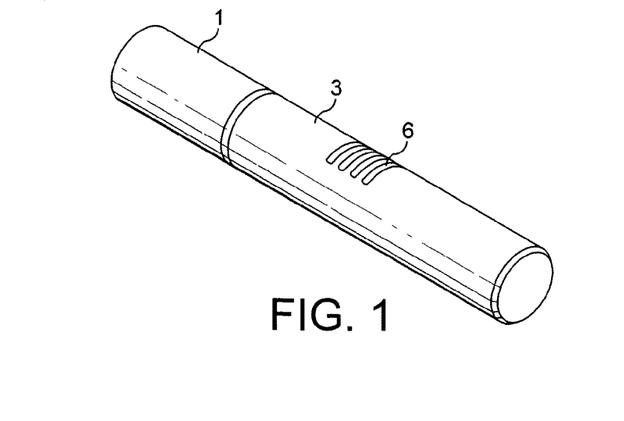
FIG. 1 is a schematic perspective view of an inhaler.
Figure 2A:
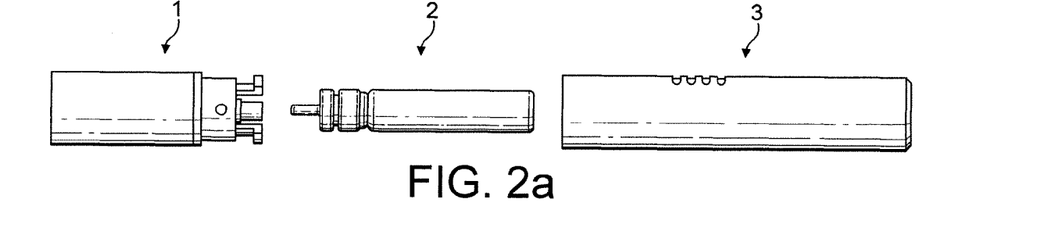
FIG. 2a is a general, exploded view of the body parts in canister of the inhaler shown in FIG. 1.
Figure 2B:
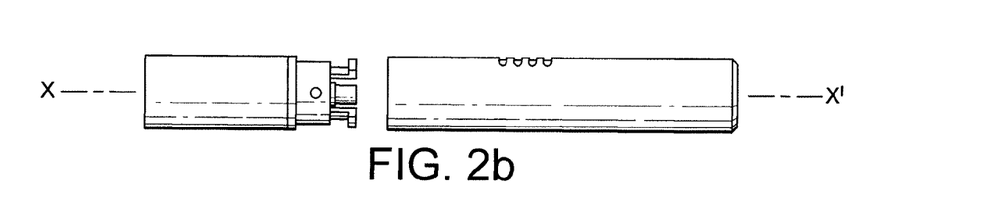
FIGS. 2b and 2c illustrate the body parts of the container in plan and perspective views respectively.
Figure 2C:
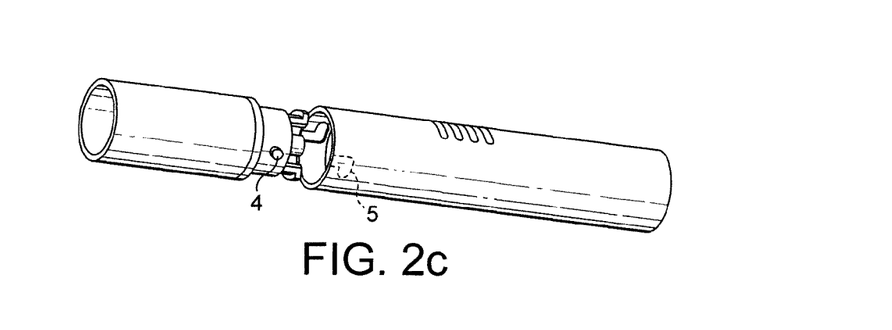

Referring to FIG. 1, a portable handheld breath-actuated inhaler is illustrated that is generally cylindrical in configuration, which can be used as a substitute for a cigarette, cigar or like smoking article. As shown in FIGS. 1 and 2, the inhaler comprises a first body portion 1 that acts as a mouthpiece, a generally cylindrical canister 2 that contains pressurized fluid containing nicotine and a second body portion 3 in which the canister 2 is received to deliver a nicotine aerosol into the mouthpiece provided by the first body part 1.

As explained in more detail hereinafter, the inhaler is breath-actuated so that when a user sucks on the mouthpiece provided by body portion 1, a metered amount of nicotine aerosol spray is delivered for inhalation by the user.

Figure 3A:
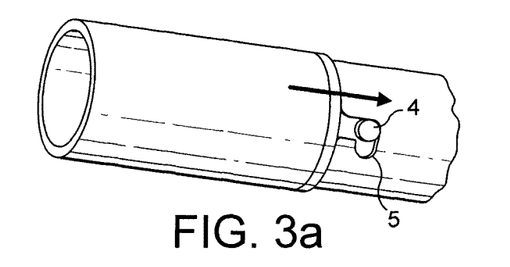
FIGS. 3a and 3b illustrate the coupling between the first and second parts of the body of the inhaler.
Figure 3B:
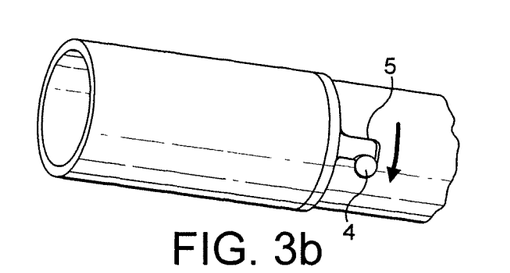

The canister 2 is interchangeable so that when it becomes emptied, it can be replaced by another. To this end, the first body portion 1 is provided with a bayonet fitting comprising lugs 4 and the second body portion is provided with corresponding L-shaped slots 5 to attach the first and second body portions 1, 3 releasably as illustrated in more detail in FIGS. 3a and 3b.

The second body portion 3 includes a pressure sensitive member, to be described in more detail hereinafter that is responsive to the user sucking on the mouthpiece 2, which in turn triggers a spring loaded trigger mechanism that drives the canister 2 towards the mouthpiece so as to release a metered amount of nicotine based aerosol spray for inhalation by the user.

Figure 4A:
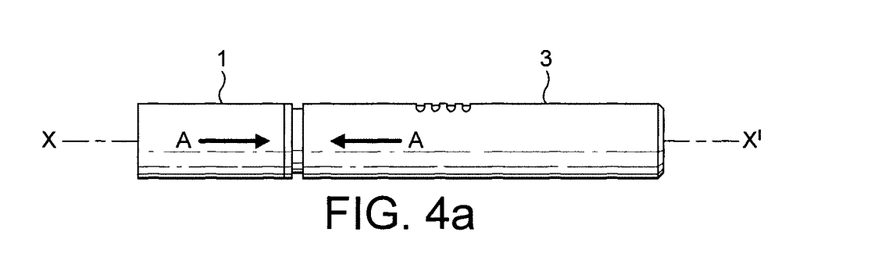
FIGS. 4a, 4b and 4c illustrate successive steps in the use of the inhaler to cock and deliver aerosol to the user.
Figure 4B:
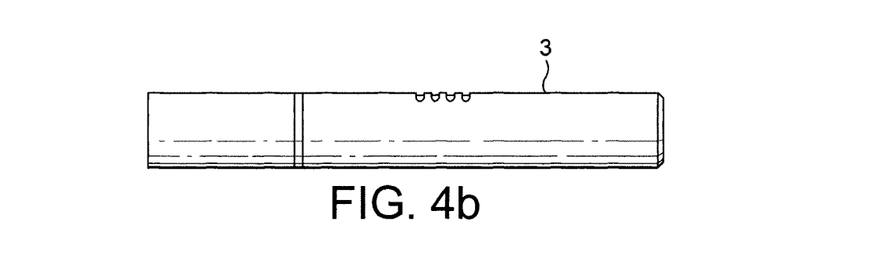

As shown in FIG. 2b, the first and second portions 1, 3 of the body are generally cylindrical and of a longitudinally constant diameter, which extend coaxially along longitudinal axis X-X'. As shown in FIG. 4, the first and second body portions 1, 3 are slidable relative to one another along the axis X-X'. Referring to FIG. 4a, the body portions 1, 3 can be slid towards one another in the direction of arrows A which, as will be explained in more detail hereinafter, stores energy in a spring within the second body portion 3 and also cocks a trigger therein. As a result, the inhaler is rendered into a loaded or cocked state as illustrated in FIG. 4b.

When the user sucks on the mouthpiece 1, air is drawn into an air inlet opening 6 in the second body portion 3 which, as will be explained hereinafter operates the pressure sensitive member within the second portion 3 of the housing so as to release the trigger and drive the spring against the canister, thereby releasing a metered amount of aerosol into the mouthpiece for the user.

Figure 4C:
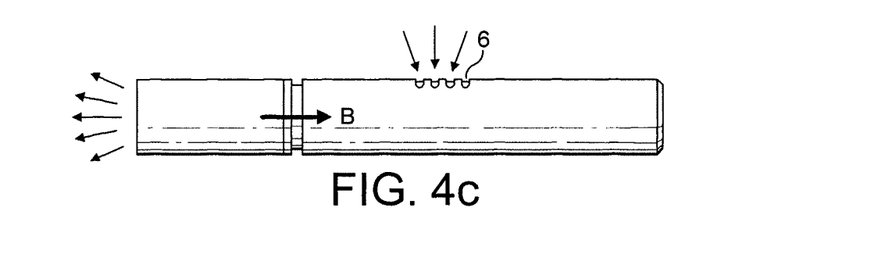
Figure 5:
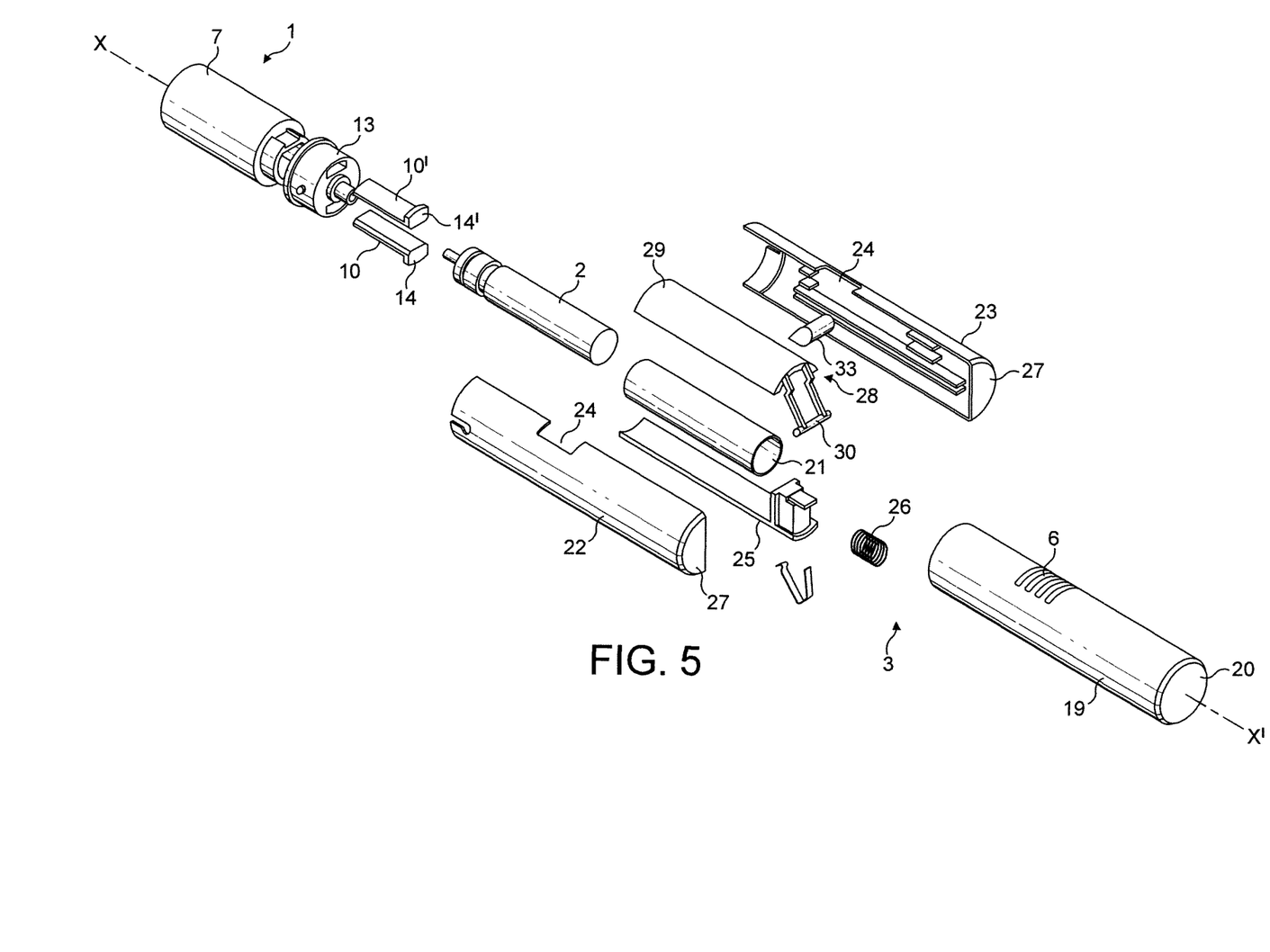
FIG. 5 is a schematic exploded view of the inhaler.

Upon release of the trigger, the second portion of the housing 3 moves away from the first portion 1 in the direction of arrow B under the action of the spring as illustrated in FIG. 4C.

The interior structure of the inhaler will now be described in more detail with reference to FIGS. 5-10A.

The first body portion 1 comprises a generally cylindrical mouthpiece 7 having a mouthpiece opening 8 and a central bore 9 that communicates with the second body portion 3. First and second axially extending guide rails 10, 10' are snap-fitted into recesses 11 through apertures 12 in a generally cylindrical nozzle attachment 13. The guide rails 10, 10' have end flanges 10A so that the nozzle attachment 13 can slide back and forth along the guide rails between a position abutting the mouthpiece 7 and a position abutting the flanges 10A so as to allow the movement in the direction of arrows A, B illustrated in FIG. 4.

The nozzle attachment 13 includes a stepped, central bore 10A to receive aerosol from the canister 2 as will be explained later, together with side apertures 15 that permit air to be drawn from the second part 3 into the mouthpiece 7 when the user sucks on the mouthpiece opening 8.

Figure 6:
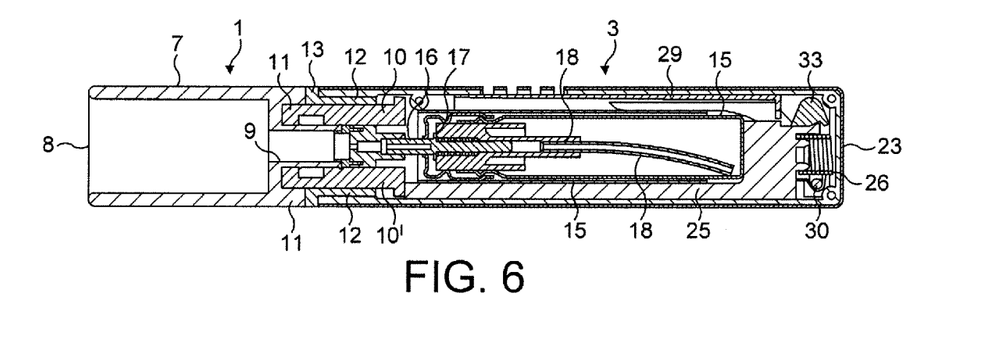
FIG. 6 is a longitudinal sectional view of the inhaler when cocked.

The canister 2 contains the product to be inhaled by the user, for example nicotine, together with a propellant such as liquid HSFA134a. The mixture of product and propellant can be selected in order to achieve a particular flavor, spray effect and performance. As illustrated in FIG. 6, which shows the canister 2 in longitudinal section, the canister comprises a generally cylindrical casing 15 with an axially extending output tube 16 that provides an outlet for the aerosol from a spring loaded valve 17 having a fluid inlet tube 18 to receive pressurized liquid from within the casing 15. The valve 17 is of the type conventionally used in pressurized spray cans and is configured so that when the outlet tube 16 is depressed inwardly, the internal spring within valve 17 is compressed so that the valve is opened to release aerosol spray through the tube 16. When the tube 16 is released, the valve 17 is urged shut by its internal spring.

As previously stated, the canister 2 is received within the second part 3 of the body. In more detail, the second body part 3 comprises a generally cylindrical outer housing shell 19 that is closed at its distal end 20, and includes the air inlet opening 6.

The canister 2 is received within a metal canister tube 21 within left and right semi cylindrical main housing parts 22, 23 that each include a cut out portion 24 that underlies the inlet 6 in the outer housing shell 19, to allow outside air to be drawn into the main housing 22, 23 through the inlet opening 6 when then user sucks on the mouthpiece 8.

The canister tube 21 rests on a drive plunger 25 received within the housing parts 22, 23. The proximal end of the drive plunger 25 can abut the end flange 10A of lowermost guide rail 10, and the distal end of the plunger 25 is generally L-shaped.

A compression spring 26 disposed between the distal end of the drive plunger 25 and distal end regions 27 of the housing parts 22, 23, and upon release, the spring drives the plunger 25 towards the lowermost drive arm 10, so as to drive the outlet tube 16 of the canister 2 into and against the step in the bore 10A on the nozzle attachment 13.

A puff-actuated trigger mechanism comprises a puff lever 28 that comprises a part-cylindrical plate 29 located within the housing parts 22, 23, beneath the inlet opening 6 in the outer housing shell 19. The puff lever 28 is pivotable within the main housing 22, 23 about an integral, depending transverse shaft 30, the ends of which are received within integral bearing bosses in the housing parts 22, 23 (not shown). As clearly shown in FIG. 9, the shaft 30 is coupled to the part cylindrical plate 29 by arms 31 that include a detent 32 that forms part of a trigger mechanism by engaging with a cam 33 that pivots about a shaft 34 journaled in the housing parts 22, 23.

Figure 9:
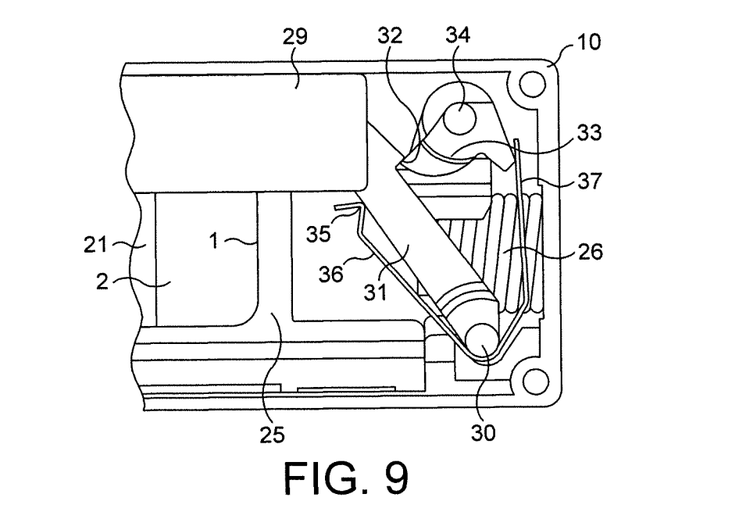
FIG. 9 is an enlarged part section of the trigger mechanism of the inhaler when cocked.
Figure 10:
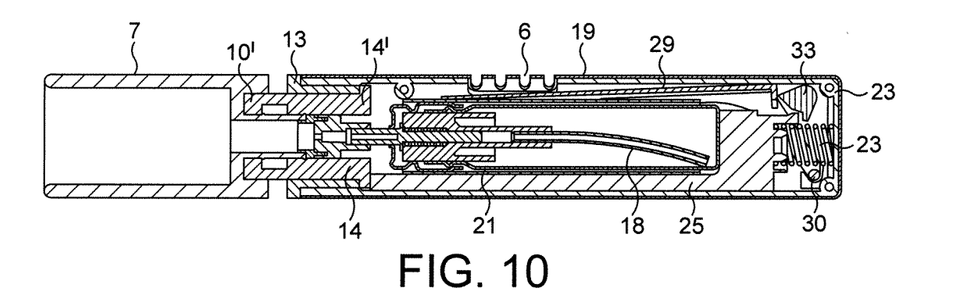
FIG. 10 is a sectional view corresponding to FIG. 6 upon release.

The trigger cocking mechanism includes a generally V-shaped leaf spring 35 has first and second arms 36, 37. The arm 36 urges the puff lever 28 such that the part cylindrical surface 29 is coaxial with the major axis X-X' of the device and underlying the inlet opening 6. The second arm 37 urges the trigger mechanism cam 32 to rotate clockwise as shown in FIG. 9 into engagement with detent 32.

Cocking

Figure 7:
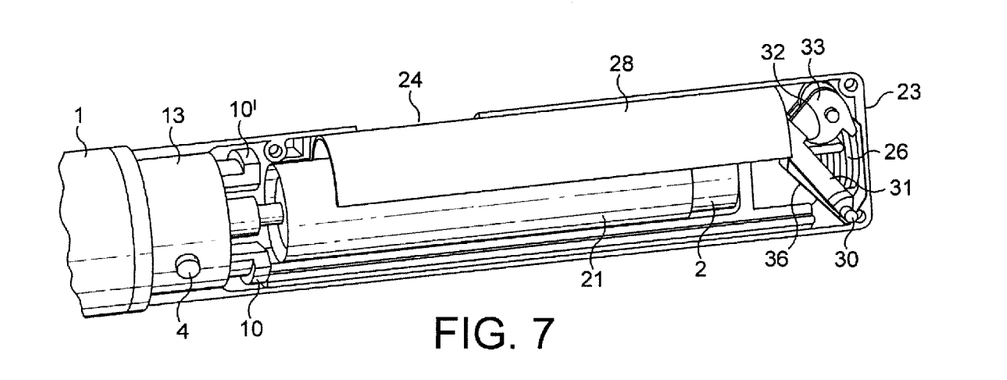
FIG. 7 is a partially cut away perspective view of the inhaler when cocked.
Figure 8:
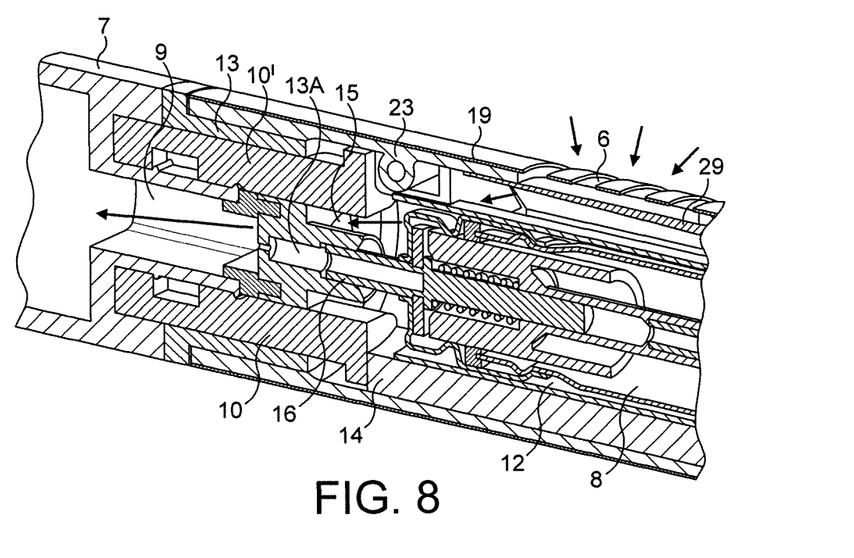
FIG. 8 is an enlarged sectional view of the inhaler in the region of the join between its first and second body parts.
Figure 12:
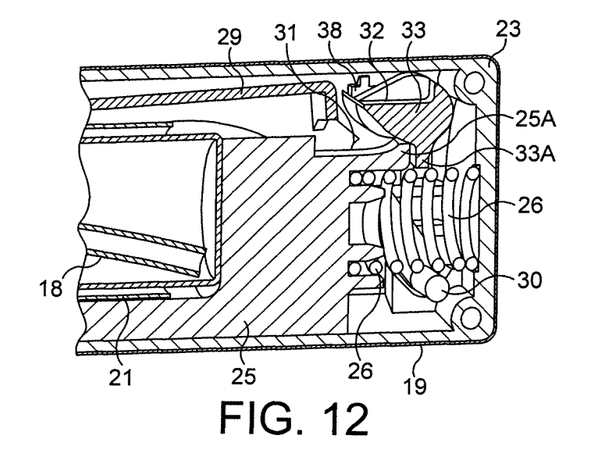
FIG. 12 is an enlarged sectional view of the trigger mechanism when released.
Figure 13:
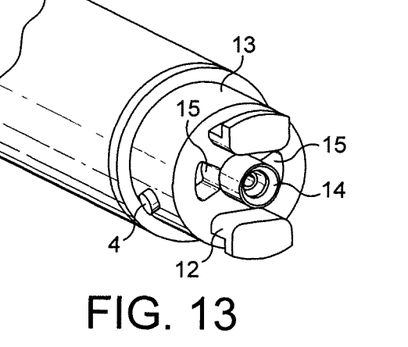
FIG. 13 is an enlarged view of the first body part showing air passageways.
Figure 14:
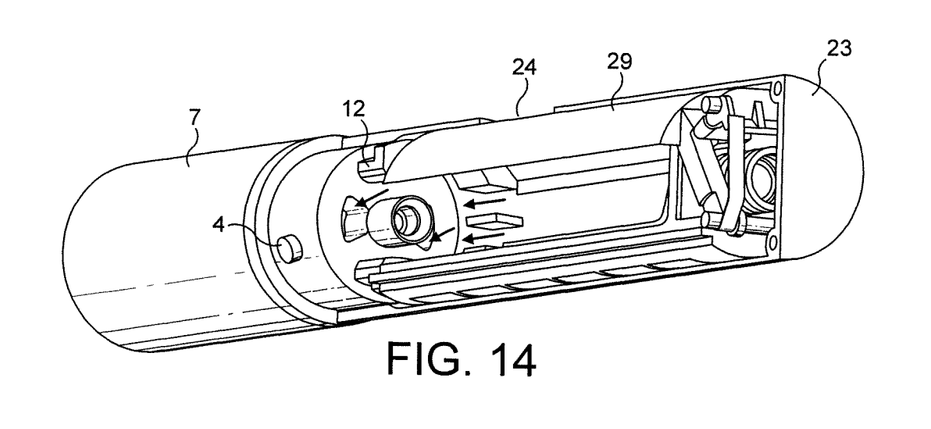
FIG. 14 is a partial sectional view of the inhaler illustrating air passageways between the first and second parts of the body.

In order to cock or prime the device, the user manually pushes the first and second body portions 1, 3 towards one another in the direction of arrows A illustrated in FIG. 4A. As a result, the spring 26, which is located between distal end 38 of the drive plunger 35 and the distal end 27 of the main body 22, 23, is compressed as illustrated in FIGS. 6, 7 and 9. Also, as shown in FIG. 12, the cam 33 is rotated about shaft 34 by portion 25A of the distal end of the drive plunger 25 engaging flange 33A on the cam 33 so that it is brought into engagement with the detent 32 on arm 31 of the puff lever 28 and is latched into engagement therewith by the action of leaf spring 35, so that the plate 29 is disposed generally parallel to and underlying the inlet opening 6.

Actuation

When the user places the mouthpiece in his or her mouth and sucks on it, air is drawn into the mouthpiece through apertures 15 in the nozzle attachment 13 from within the main housing 22, 23, which in turn draws air through the inlet aperture 6 in the outer shell 19 and through the cut out portions 24 in the main housing 22, 23. This produces a pressure differential across the plate 29 of puff lever 28, causing it to rotate inwardly of the inhaler about shaft 30, thereby disengaging the detent 32 on arm 31 from the cam 34 of the trigger mechanism.

As a result, the compressed spring 26 expands, moving the main housing 22, 23 outwardly of the mouthpiece 7 in the direction of arrow B shown in FIG. 4C, with the result that the nozzle attachment 13 slides along the drive arms 10, 10' until it engages the stops 10A.

Also, the expansion of the released spring 26 drives the canister tube 21 along with canister 2 towards the nozzle attachment 13, The outlet tube 16 abuts the step in bore 14 in nozzle attachment 13 and so is driven inwardly of the canister 2 so as to open canister valve 17 and release spray from within the canister into bore 9 through bore 14 and hence into the mouthpiece 7 for inhalation by the user.

Figure 11:
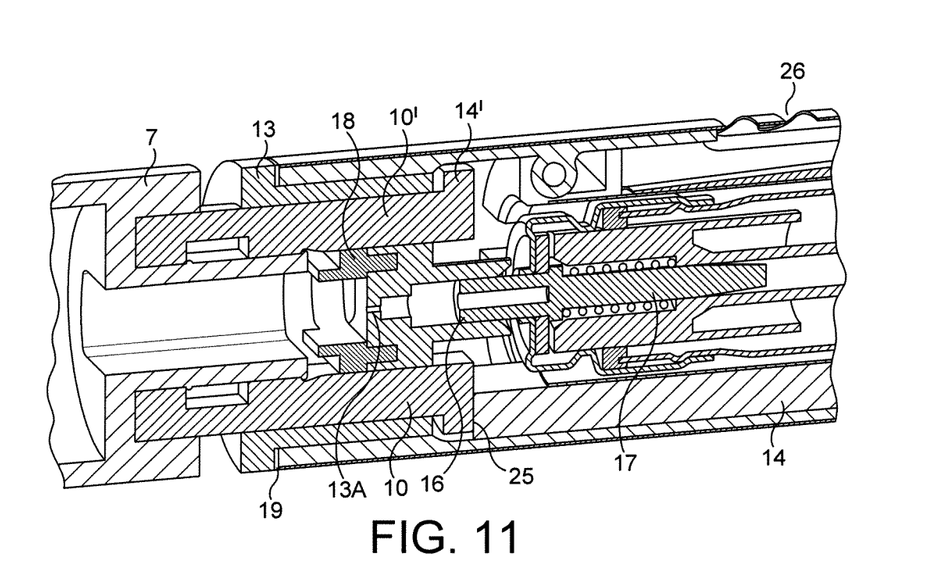
FIG. 11 is an enlarged view of the join between the first and second body parts upon release.

Thereafter, the spring loaded valve 17 causes the canister 2 recoils against the force of spring 26, so as to move in the direction of arrow B (FIG. 4C) away from the nozzle attachment 13 such that valve 17 closes. As a result, a metered puff of aerosol spray is delivered from the canister 2 into the mouthpiece after which the valve 17 closes. Thus, in operation, the second body portion 3 of the inhaler moves from the initial, cocked position shown in FIGS. 6, 7, 8 and 9 to a released position shown in FIGS. 10 and 11, from which it can be cocked again as described previously, ready to release a further, breath actuated puff of the aerosol spray.

The cocking of the inhaler after each inhalation of aerosol in some respects is similar to the manual handling procedure followed by a smoker of a conventional cigarette in the sense that the breath actuation of the cocked inhaler corresponds to drawing on a cigarette by coordinates the inhalation with the dispensing of the product. Also, the subsequent removal of the inhaler from the mouth and re-cocking corresponds to a manual action which in some respects is similar to the use of an ash tray for a conventional cigarette.

Many modifications and variations fall within the scope of the invention and for example, although the described example of inhaler is generally cylindrical with a constant diameter along its length, it would be possible to taper the diameter for example, in the region of the mouthpiece. The dispensing configuration of the inhaler has the advantage that it is manually cocked and uses a spring and thus avoids the need for batteries and electronics for controlling the dispensation of the aerosol.

The invention claimed is:

1. A portable, handheld breath-actuated inhaler comprising:
    a body to receive a canister of pressured fluid to be inhaled in an aerosol by a user,
    a mouthpiece configured to deliver an amount of the aerosol to the mouth of the user,
    a trigger mechanism operable to be cocked into a configuration ready for releasing pressurized fluid from the canister, and
    a pressure sensitive member operable to release the cocked trigger in response to the user sucking on the body so as to deliver the fluid to the mouthpiece,
    wherein the body includes an inlet aperture to allow air to be drawn therein in response to sucking on the mouthpiece, to be mixed with the fluid delivered from the canister into the mouthpiece, and
    wherein the pressure sensitive member includes a puff lever biased to at least partially close the inlet aperture, the puff lever being configured to be rotated by air drawn into the body when the user sucks on the mouthpiece, and thereby release the cocked trigger mechanism.

2. The inhaler according to claim 1
    wherein the body includes first and second portions moveable relative to one another to cock the trigger mechanism, and a spring to store energy upon relative movement of the first and second parts by the user to cock the trigger mechanism.

3. The inhaler according to claim 2
    wherein the spring is configured to drive against the canister to cause a release of fluid from the canister upon release of the trigger mechanism.

4. The inhaler according to claim 2
    wherein the first and second body portions are generally cylindrical about a common longitudinal axis and moveable axially relative to one another.

5. The inhaler according to claim 4
    wherein one of the body portions includes the mouthpiece and the other is adapted to receive the canister and includes the spring and trigger mechanism.

6. The inhaler according to claim 2
    wherein the first and second body portions are moveable towards one another to cock the trigger mechanism and compress the spring, and moveable away from one another when the trigger is released by the pressure sensitive member so as to elongate the body.

7. The inhaler according to claim 2
    wherein the second body portion includes a nozzle attachment with an opening to deliver fluid from the canister to the mouthpiece, the nozzle attachment being mounted for limited sliding movement on the first body portion for cocking and release of the trigger mechanism.

8. The inhaler according to claim 1 and including the canister.

9. The inhaler according to claim 8
    wherein the canister contains a nicotine containing fluid.

10. A portable, handheld breath-actuated inhaler comprising:
    a body to receive a canister of pressured fluid to be inhaled in an aerosol by a user,
    a mouthpiece configured to deliver an amount of the aerosol to the mouth of the user,
    a trigger mechanism operable to be cocked into a configuration ready for releasing pressurized fluid from the canister, and
    a pressure sensitive member operable to release the cocked trigger in response to the user sucking on the body so as to deliver the fluid to the mouthpiece,
    wherein the body includes first and second portions that are generally cylindrical about a common longitudinal axis and axially moveable relative to one another.

11. The inhaler according to claim 10,
    wherein one of the body portions includes the mouthpiece and the other is adapted to receive the canister and includes the trigger mechanism.

12. The inhaler according to claim 10,
    wherein the first and second body portions are moveable towards one another to cock the trigger mechanism, and moveable away from one another when the trigger is released by the pressure sensitive member so as to elongate the body.

13. The inhaler according to claim 10,
    wherein the second body portion includes a nozzle attachment with an opening to deliver fluid from the canister to the mouthpiece, the nozzle attachment being mounted for limited sliding movement on the first body portion for cocking and release of the trigger mechanism.

14. The inhaler according to claim 10,
    wherein the body includes an inlet aperture to allow air to be drawn therein in response to sucking on the mouthpiece, to be mixed with the fluid delivered from the canister into the mouthpiece, and
    wherein the pressure sensitive member includes a puff lever biased to at least partially close the inlet aperture, the puff lever being configured to be rotated by air drawn into the body when the user sucks on the mouthpiece, and thereby release the cocked trigger mechanism.

15. The inhaler according to claim 10 and including the canister.

16. The inhaler according to claim 10, wherein the canister contains a nicotine containing fluid.

17. A portable, handheld breath-actuated inhaler comprising:
    a body to receive a canister of pressured fluid to be inhaled in an aerosol by a user,
    a mouthpiece configured to deliver an amount of the aerosol to the mouth of the user,
    a trigger mechanism operable to be cocked into a configuration ready for releasing pressurized fluid from the canister, and
    a pressure sensitive member operable to release the cocked trigger in response to the user sucking on the body so as to deliver the fluid to the mouthpiece,
    wherein the body includes first and second portions that are generally cylindrical about a common longitudinal axis and axially moveable relative to one another, and
    wherein one of the body portions includes the mouthpiece and the other is adapted to receive the canister and includes the trigger mechanism.

18. The inhaler according to claim 17,
wherein the first and second body portions are moveable towards one another to cock the trigger mechanism, and moveable away from one another when the trigger is released by the pressure sensitive member so as to elongate the body.

19. The inhaler according to claim 17,
wherein the second body portion includes a nozzle attachment with an opening to deliver fluid from the canister to the mouthpiece, the nozzle attachment being mounted for limited sliding movement on the first body portion for cocking and release of the trigger mechanism.

20. The inhaler according to claim 17,
wherein the body includes an inlet aperture to allow air to be drawn therein in response to sucking on the mouthpiece, to be mixed with the fluid delivered from the canister into the mouthpiece, and
wherein the pressure sensitive member includes a puff lever biased to at least partially close the inlet aperture, the puff lever being configured to be rotated by air drawn into the body when the user sucks on the mouthpiece, and thereby release the cocked trigger mechanism.

21. The inhaler according to claim 17 and including the canister.

22. The inhaler according to claim 17, wherein the canister contains a nicotine containing fluid.

23. A portable, handheld breath-actuated inhaler comprising:
a body to receive a canister of pressured fluid to be inhaled in an aerosol by a user,
a mouthpiece configured to deliver an amount of the aerosol to the mouth of the user,
a trigger mechanism operable to be cocked into a configuration ready for releasing pressurized fluid from the canister, and
a pressure sensitive member operable to release the cocked trigger in response to the user sucking on the body so as to deliver the fluid to the mouthpiece,
wherein the body includes first and second portions moveable relative to one another, and
wherein the second body portion includes a nozzle attachment with an opening to deliver fluid from the canister to the mouthpiece, the nozzle attachment being mounted for limited sliding movement on the first body portion for cocking and release of the trigger mechanism.

24. The inhaler according to claim 23,
wherein one of the body portions includes the mouthpiece and the other is adapted to receive the canister and includes the trigger mechanism.

25. The inhaler according to claim 23,
wherein one of the body portions includes the mouthpiece and the other is adapted to receive the canister and includes the trigger mechanism.

26. The inhaler according to claim 23,
wherein the first and second body portions are moveable towards one another to cock the trigger mechanism, and moveable away from one another when the trigger is released by the pressure sensitive member so as to elongate the body.

27. The inhaler according to claim 23,
wherein the body includes an inlet aperture to allow air to be drawn therein in response to sucking on the mouthpiece, to be mixed with the fluid delivered from the canister into the mouthpiece, and
wherein the pressure sensitive member includes a puff lever biased to at least partially close the inlet aperture, the puff lever being configured to be rotated by air drawn into the body when the user sucks on the mouthpiece, and thereby release the cocked trigger mechanism.

28. The inhaler according to claim 23 and including the canister.

29. The inhaler according to claim 23, wherein the canister contains a nicotine containing fluid.

30. A portable, handheld breath-actuated inhaler comprising:
a body to receive a canister of pressured nicotine containing fluid to be inhaled in an aerosol by a user,
a mouthpiece configured to deliver an amount of the aerosol to the mouth of the user,
a trigger mechanism operable to be cocked into a configuration ready for releasing pressurized nicotine containing fluid from the canister, and
a pressure sensitive member operable to release the cocked trigger in response to the user sucking on the body so as to deliver the nicotine containing fluid to the mouthpiece.

31. The inhaler according to claim 30,
wherein the body includes first and second portions moveable relative to one another.

32. The inhaler according to claim 31,
wherein the first and second body portions are generally cylindrical about a common longitudinal axis and moveable axially relative to one another.

33. The inhaler according to claim 31,
wherein one of the body portions includes the mouthpiece and the other s adapted to receive the canister and includes the trigger mechanism.

34. The inhaler according to claim 31,
wherein the first and second body portions are moveable towards one another to cock the trigger mechanism, and moveable away from one another when the trigger is released by the pressure sensitive member so as to elongate the body.

35. The inhaler according to claim 31,
wherein the second body portion includes a nozzle attachment with an opening to deliver the nicotine containing fluid from the canister to the mouthpiece, the nozzle attachment being mounted for limited sliding movement on the first body portion for cocking and release of the trigger mechanism.

36. The inhaler according to claim 31,
wherein the body includes an inlet aperture to allow air to be drawn therein in response to sucking on the mouthpiece, to be mixed with the nicotine containing fluid delivered from the canister into the mouthpiece, and
wherein the pressure sensitive member includes a puff lever biased to at least partially close the inlet aperture, the puff lever being configured to be rotated by air drawn into the body when the user sucks on the mouthpiece, and thereby release the cocked trigger mechanism.

* * * * *

UNITED STATES PATENT AND TRADEMARK OFFICE
CERTIFICATE OF CORRECTION

PATENT NO.         : 8,495,998 B2                                        Page 1 of 1
APPLICATION NO.    : 12/486476
DATED              : July 30, 2013
INVENTOR(S)        : Steven Michael Schennum et al.

It is certified that error appears in the above-identified patent and that said Letters Patent is hereby corrected as shown below:

In the Claims

Column 8, line 35, "- and the other s adapted -" should read -- and the other is adapted --

Signed and Sealed this
Twenty-second Day of April, 2014

Michelle K. Lee
*Deputy Director of the United States Patent and Trademark Office*